United States Patent
Bruckheimer (10) Patent No.: US 7,497,873 B1
(45) Date of Patent: Mar. 3, 2009

(54) INTRAVASCULAR DEVICE AND METHOD USING IT

(75) Inventor: Elchanan Bruckheimer, Zichron Yaakov (IL)

(73) Assignee: Rafael Medical Technologies Inc., Dover, DE (US)

( * ) Notice: Subject to any disclaimer, the term of this patent is extended or adjusted under 35 U.S.C. 154(b) by 324 days.

(21) Appl. No.: 10/069,618

(22) PCT Filed: Sep. 10, 2000

(86) PCT No.: PCT/IL00/00553

§ 371 (c)(1), (2), (4) Date: Jun. 3, 2002

(87) PCT Pub. No.: WO01/19231

PCT Pub. Date: Mar. 22, 2001

(30) Foreign Application Priority Data

Sep. 10, 1999 (IL) .................................. 131863

(51) Int. Cl. *A61F 2/06* (2006.01)
(52) U.S. Cl. .................................. 623/1.18; 623/1.22
(58) Field of Classification Search ................. 606/113, 606/114, 191–200; 604/96; 623/1.18, 1.22
See application file for complete search history.

(56) References Cited

U.S. PATENT DOCUMENTS

| | | | |
|---|---|---|---|
| 4,425,908 A | | 1/1984 | Simon |
| 5,053,008 A | | 10/1991 | Bajaj |
| 5,098,440 A | * | 3/1992 | Hillstead ............... 606/108 |
| 5,171,233 A | * | 12/1992 | Amplatz et al. ........... 606/113 |
| 5,258,000 A | * | 11/1993 | Gianturco ............... 606/151 |
| 5,312,416 A | * | 5/1994 | Spaeth et al. ............ 606/114 |
| 5,334,217 A | * | 8/1994 | Das ................... 606/151 |
| 5,423,851 A | | 6/1995 | Samuels |
| 5,643,317 A | * | 7/1997 | Pavcnik et al. ........... 606/213 |
| 5,720,754 A | * | 2/1998 | Middleman et al. ........ 606/127 |
| 5,769,816 A | * | 6/1998 | Barbut et al. ............ 606/200 |
| 5,800,525 A | * | 9/1998 | Bachinski et al. ......... 623/1.1 |
| 5,846,260 A | * | 12/1998 | Maahs ................. 606/200 |
| 5,904,690 A | * | 5/1999 | Middleman et al. ........ 606/113 |
| 6,004,330 A | * | 12/1999 | Middleman et al. ........ 606/127 |
| 6,120,524 A | * | 9/2000 | Taheri ................. 606/213 |
| 6,152,144 A | * | 11/2000 | Lesh et al. ............. 128/898 |
| 6,355,052 B1 | * | 3/2002 | Neuss et al. ............ 606/213 |
| 6,488,700 B2 | * | 12/2002 | Klumb et al. ........... 623/1.12 |
| 6,740,111 B1 | * | 5/2004 | Lauterjung ............. 623/1.1 |
| 2005/0203568 A1 | * | 9/2005 | Burg et al. ............. 606/200 |

* cited by examiner

*Primary Examiner*—Todd E Manahan
*Assistant Examiner*—Amy T Lang
(74) *Attorney, Agent, or Firm*—Mark M. Friedman (57) ABSTRACT

An intravascular device for minimally invasive deployment within a vessel includes a closed loop of flexible material configured to assume a first state in which the closed loop is folded on itself and straightened to allow delivery through a minimally invasive delivery system. When deployed, the loop assumes a second substantially ring-shaped state to become lodged against an inner wall of the vessel. The loop is preferably formed from a shape memory alloy preset to the second state and temporarily deformed to assume said first state during deployment.

13 Claims, 6 Drawing Sheets

INTRAVASCULAR DEVICE AND METHOD USING IT

FIELD AND BACKGROUND OF THE INVENTION

This invention relates to intravascular devices, and to methods of treatment using such devices.

Many forms of congenital heart disease result in shunting of the blood from the high resistance left-ventricle-aorta circuit into the low resistance right ventricle pulmonary artery circuit. This blood returns to the heart instead of going to the body and overloads the left ventricle causing congestion. This condition, known as congestive heart failure, is associated with difficulty in breathing and increased energy expenditure causing failure to thrive in the case of an infant. An additional and no less important aspect of such a shunt is the exposure of the lung blood vessels to high flow rates and pressures which eventually cause irreversible damage.

The solutions to the problems imposed by a large shunt include: medication to reduce the shunt, and repair of the heart defect by surgery of pulmonary artery banding [PAB]. This latter option, PAB, is employed today in cases when repair of the defect is not possible due to defect types or infant size or as a first stage palliative procedure for complex congenital disease.

PAB involves a surgical procedure under general anesthesia during which the chest is opened and a band of synthetic material is placed around the main pulmonary artery and tightened relatively arbitrarily to increase the resistance to flow. During the surgery pressures and oxygen saturation can be measured to evaluate the hemodynamic effect of banding however this does not always correlate well with findings after surgery. Apart from the general disadvantages of surgery [wound, scar, possibility of infection], surgical PAB can lead to distortion of the pulmonary arteries due to band migration. In addition if the band is too tight or loose it cannot be adjusted without additional surgery. Once the band has served it's purpose it has to be removed by surgery and the damaged area of the pulmonary artery is repaired. This is usually performed during the repair of the underlying defect.

The fields of cardiac catheterization and angiography have changed immensely with the introduction of transcatheter therapeutic/interventional techniques. It is now possible to close cardiac defects, relieve narrowings of systemic, pulmonary and coronary arteries, occlude accessory vessels, biopsy the heart and open valves through a small entry site, less than 2.5-3 mm, in the groin. These procedures obviate the need for surgery, including open heart, while affording excellent results. This minimally invasive approach avoids scarring and affords a more rapid recovery. The transcatheter procedure is usually performed on an overnight of same day basis thereby significantly reducing hospital stay and costs. A common example is the use of stents instead of bypass surgery in coronary artery stenosis.

An additional form of disease amenable to transcatheter therapy is pulmonary embolism. This condition is the result of blood clots which form in a vein of the lower part of the body and break loose, migrating to the lungs. One form of treatment of these emboli is by inserting a filter in a blood vessel such as the vena cava to interrupt the travel of these emboli. One such filter is disclosed in U.S. Pat. No. 4,425,908. Devices currently in use require relatively large sheaths for insertion, and are usually irretrievable.

SUMMARY OF THE INVENTION

It is an object of the present invention to provide an intravascular device which can be delivered to a desired location by use of a catheter.

It is a further object of the invention to provide a method for treatment of certain intravascular diseases using an intravascular device which can be delivered to a desired location by use of a catheter.

In one aspect of the invention, there is provided an intravascular device for positioning in a blood vessel and capable of being delivered to the blood vessel in a catheter, comprising a platform on which functional structures may be mounted, or with which they may be integrally formed. The platform is preferably composed of a shape memory alloy, such as Nitinol, and is configured to form a collapsed folded conformation in which it can be straightened for transcatheter delivery, and is further configured to subsequently form an expanded ring conformation. The properties and design considerations for shape memory alloys are now well documented and will not be discussed here in detail.

Thus, according to the teachings of the present invention there is provided an intravascular device for minimally invasive deployment within a vessel, the intravascular device comprising a closed loop of flexible material configured to assume a first state in which the closed loop is folded on itself and straightened to allow delivery through a minimally invasive delivery system and, when deployed, assumes a second substantially ring-shaped state to become lodged against an inner wall of the vessel.

According to a further feature of the present invention, the closed loop is formed from a shape-memory alloy preset to the second substantially ring-shaped state, the closed loop being subsequently deformed to assume the first state prior to delivery.

According to a further feature of the present invention, the substantially ring-shaped state is implemented with a curvature configured such that advancing of the loop in a feed direction from a delivery system results in deployment of the loop in a direction generally perpendicular to the feed direction.

In the present disclosure, the following terms have the indicated meanings:

platform—a supporting structure on which functional structures may be mounted, attached or integrally formed. The platform will generally be fixable to the walls of the blood vessel. The platform itself generally does not have a function other than to support other functional structures. Examples of functional structures which may be supported by the platform include, but are not limited to, a pulmonary artery band for regulating blood flow, a filter for emboli and a valve.

ring conformation—a circular band having an internal bore.

shape memory alloy—a metal alloy which exhibits shape memory properties, namely, which returns to a predefined shape when exposed to a temperature above a given phase transformation temperature. As is well known for minimally invasive medical procedures, the shape memory alloy may advantageously be designed to as to be stored in a deformed state at room temperature while reverting to its predefined shape at body temperature.

Shape memory alloys compatible with the device of the invention may be based on various metals such as iron, copper or nickel, as long as they are biocompatible. A preferred shape memory alloy is Nitinol, which is made from nickel and titanium in approximately equiatomic amounts or a slight increase of nickel. A description of Nitinol may be found, inter alia, in U.S. Pat. No. 4,425,908 whose contents are incorporated herein by reference. Small changes [less than 1%] in the percentage of nickel in the alloy confer large changes in the properties of the alloy, particularly with respect to the transformation temperature. A preferred Nitinol alloy will comprise a weight percentage of 55-56% nickel in order to have shape memory and superelastic properties at body temperature. A most preferred alloy will comprise 55.1-55.6% nickel.

The use of a shape memory alloy imparts to the device the property of retrievability. The latter is of considerable importance in transcatheter implantations of expanding devices since the now expanded device usually makes transcatheter removal unfeasible, even after a short period of time. Complications of implantation, particularly incorrect positioning or migration, may require removal of the device and repositioning. If the device cannot be collapsed down to its original size and reinserted into the delivery sheath, then its removal by a transcatheter method may be impossible and surgery required. This can be avoided by using the device of the invention.

In a preferred embodiment, the platform of the device comprises a breakable section, that is, a portion which allows a gap to be introduced into the continuity of the ring, as will be further exemplified below. This facilitates cancellation of the effect of the device in situ by breaking it, in a case where the device is no longer needed.

In another aspect of the invention, there is provided a method for reducing the diameter of a blood vessel comprising:
(a) inserting into a catheter a intravascular platform as defined above in a collapsed conformation, wherein an inflatable band in an uninflated state is mounted on the platform;
(b) delivering the device to the blood vessel by introducing the catheter into the blood vessel;
(c) ejecting the device out of the catheter into the lumen of the blood vessel, whereby the platform assumes an expanded ring conformation; and
(d) inflating the inflatable band.

In a still further aspect of the invention, there is provided a method for filtering emboli in the blood stream comprising:
(a) inserting into a catheter a intravascular platform as defined above in a collapsed conformation, wherein a filter is mounted on, or integrally formed with, the platform;
(b) delivering the device to the blood vessel by introducing the catheter into the blood vessel; and
(c) ejecting the device out of the catheter into the lumen of the blood vessel, whereby the platform assumes an expanded conformation.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 3A and 3B are enlarged sectional views of the device of FIG. 1, FIG. 3A is a front view and FIG. 3B is a side view 90° perpendicular to FIG. 3A;

FIG. 7 illustrates a further embodiment of the platform of the invention; 7A is before expansion and 7B is after expansion;

FIG. 8 illustrates a still further embodiment of the platform of the invention; 8A is before expansion and 8B is after expansion;

DESCRIPTION OF THE PREFERRED EMBODIMENTS

Figure 1:
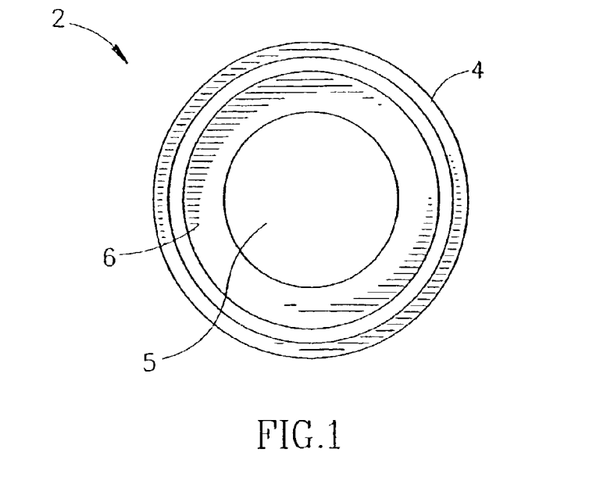
FIG. 1 is a sectional front view of one embodiment of the device of the invention.

Referring now to FIG. 1, there is illustrated one embodiment of an intravascular device according to the invention, being an intravascular pulmonary artery band, generally designated 2. The device is shown in its expanded conformation, and comprises a ring-shaped platform 4 defining an inner aperture or bore 5. An inflatable annular band 6 is coaxially mounted on the platform 4 within the aperture 5, the width of the band correspondingly reducing the diameter of the aperture. In this embodiment, the device functions as an internal transcatheter pulmonary artery band for use in the treatment of congestive heart failure due to congenital heart disease. The ring fixes the band into place by exerting pressure on the inner pulmonary artery wall.

The platform portion of the device is in a ring shape in the expanded conformation. The dimensions of the ring may easily be determined by the skilled man of the art, depending on the dimensions of the blood vessel to be occluded, for example by biplane angiography. Preferably, the ring diameter will be approximately 2 mm larger than the native pulmonary artery internal diameter. For example, if the artery diameter is 8 mm, the ring diameter will be 10 mm. Each additional size may be 2 mm larger, e.g. 12 mm, 14 mm, 16 mm etc., to accommodate for larger pulmonary artery diameters.

Figure 2A:
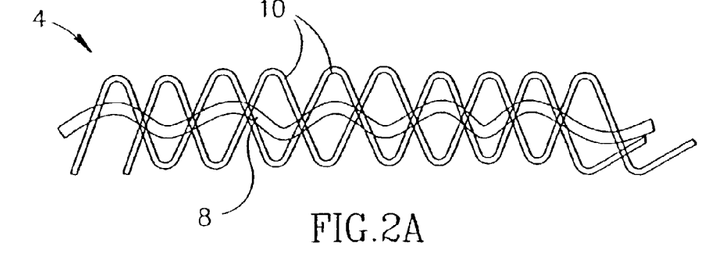
FIG. 2A is an enlarged partial view of the platform portion of the device of FIG. 1.
Figure 2B:
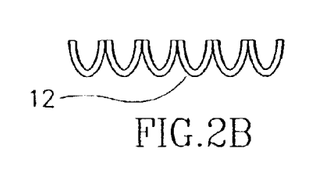
FIGS. 2B, 2C and 2D are enlarged partial views of portions of the view of FIG. 2A.

The platform 4 is composed of a shape memory alloy such as, e.g., Nitinol. The structure of the platform may be composed of one or more strands of Nitinol of varying diameters. One example of the structure of the ring is shown in FIG. 2A, which illustrates one thick 8 and two thin 10 Nitinol strands interwoven into a lattice. In many cases, slight oversizing of the ring structure is sufficient to retain the device in place. The thicker strand may optionally attach to the inner wall of the pulmonary artery by having a serrated, bumpy edge 12 (FIG.

Figure 2C:
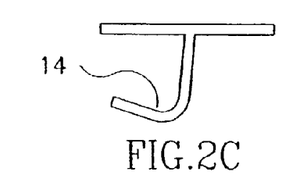
Figure 2D:
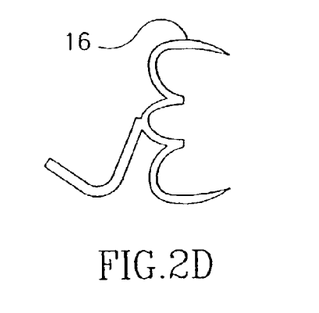

2B). Additionally, or alternatively, further retention may optionally be provided by provision of several small hooks 14 (FIG. 2C) which penetrate the inner lining of the artery. Deep penetration of the artery wall by the hooks is prevented by the adjacent loops 16 of the Nitinol strand which "cushion" the band against the arterial wall (FIG. 2D).

Figure 3A:
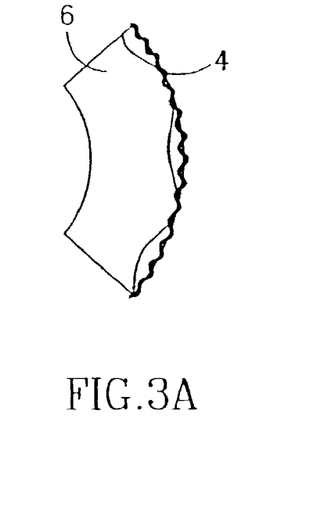
Figure 3B:
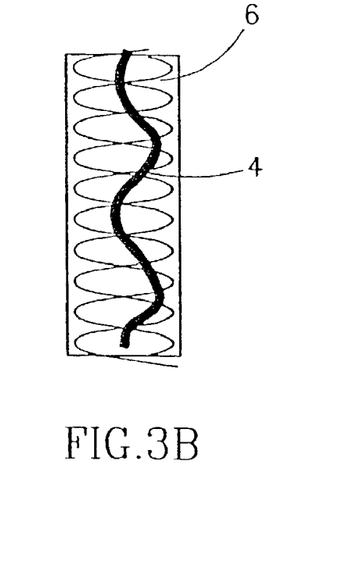

The band 6 may be composed of any flexible material which does not interact with the blood. To form an adjustable band, balloons may be attached to the Nitinol ring. These balloons will preferably be composed of an inert, biocompatible material such as silicon. The attachment of the band to the platform is illustrated in FIG. 3. In a preferred embodiment, the platform becomes part of the silicone balloon on its lateral aspect by having the balloon "melted" on during device manufacture.

Figure 4:
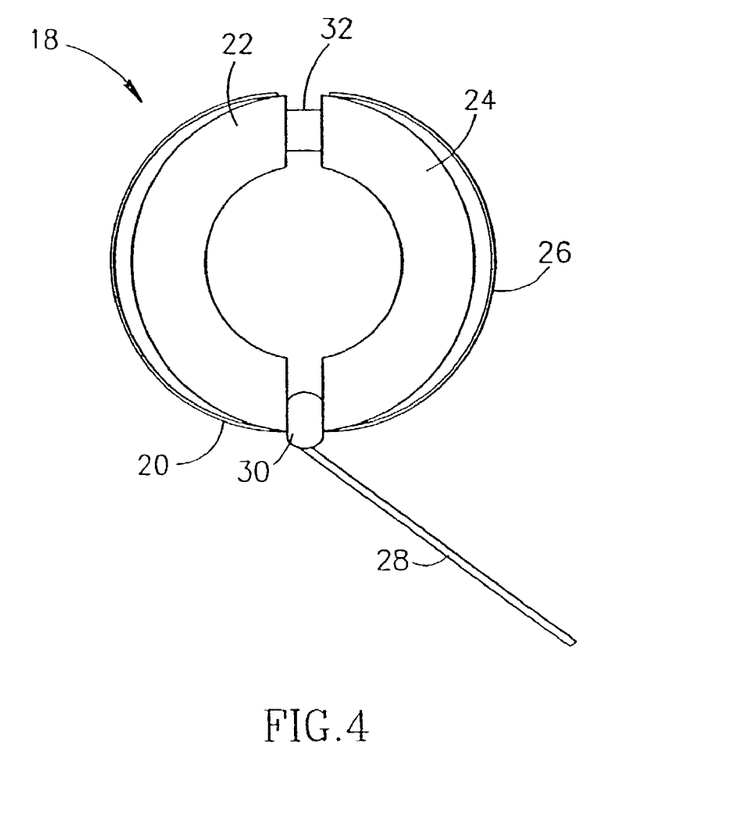
FIG. 4 is a sectional plan view illustrating another embodiment of the device of the invention in an expanded conformation.
Figure 5:
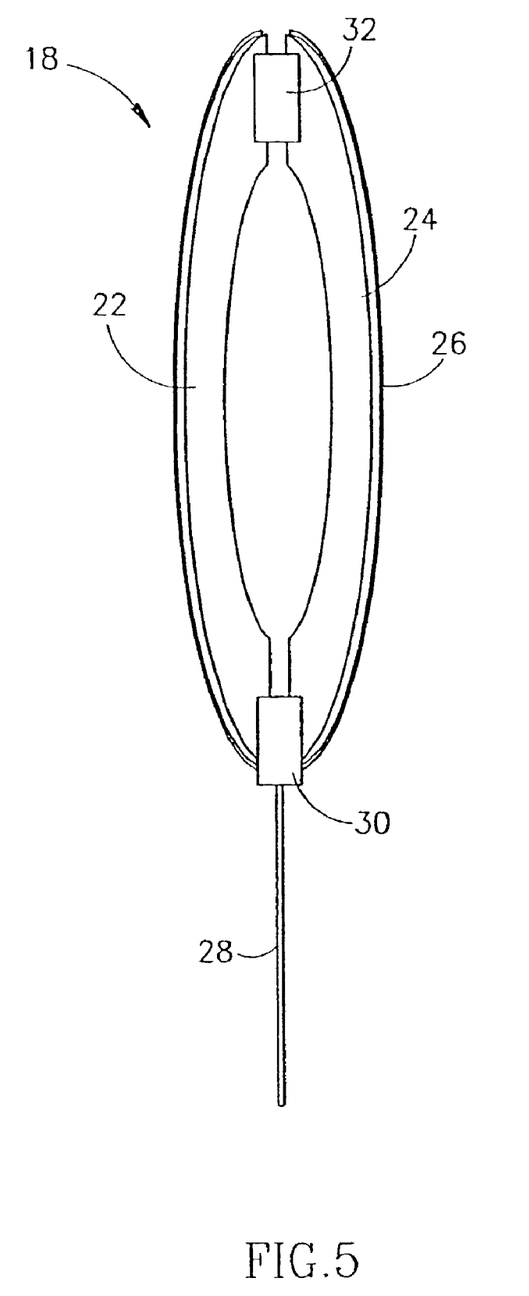
FIG. 5 shows the embodiment of FIG. 4 in a collapsed conformation.

The band may be comprised of one or more coupled inflatable balloons. FIGS. 4 and 5 illustrate one embodiment of the invention in which the device 18 comprises a band 20, consisting of two linked sausage-shaped balloons 22 & 24, mounted on a platform 26. The balloons are expanded by pushing fluid into them via a feeding catheter 28 which feeds the balloons through an elastic collar 30 which is attached to the balloons. The fluid may be isotonic saline at body temperature or a colloid at higher osmotic pressure so that fluid will not seep out. Preferably, the fluid is saline.

The collar is held open by a reinforced end region of the feeding catheter which extends through an aperture in the center of the collar. The balloons are joined by a connector 32 which may open at a predetermined pressure [e.g. 1-2 atms] to allow for the second balloon to be expanded, if required. The balloons may also be concentrically positioned within the platform (see FIG. 6D). Thus, the diameter of the band may be adjusted, depending on the hemodynamic status of the blood vessel. The decision whether to further expand or reduce the size of the balloons [by feeding or withdrawing fluid] is determined by hemodynamic measurements taken during band implantation. In order to insert the device in a catheter, the device is collapsed into its folded conformation (FIG. 5), with the band in an uninflated state.

Figure 6A:
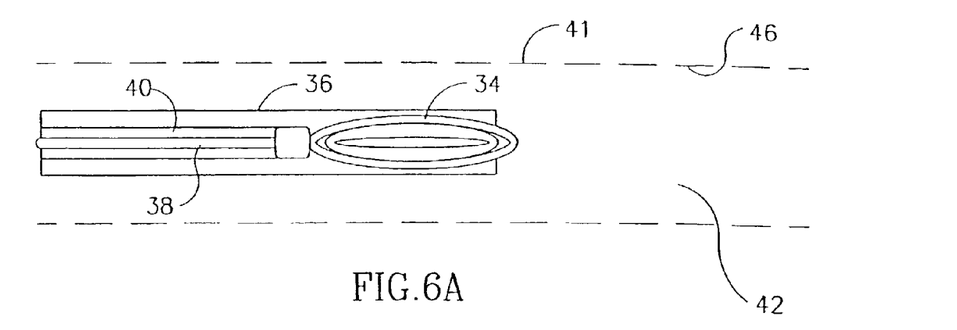
FIGS. 6A, 6B, 6C and 6D illustrate a schematic representation of the delivery of the device of the invention to a desired site in a blood vessel.
Figure 6B:
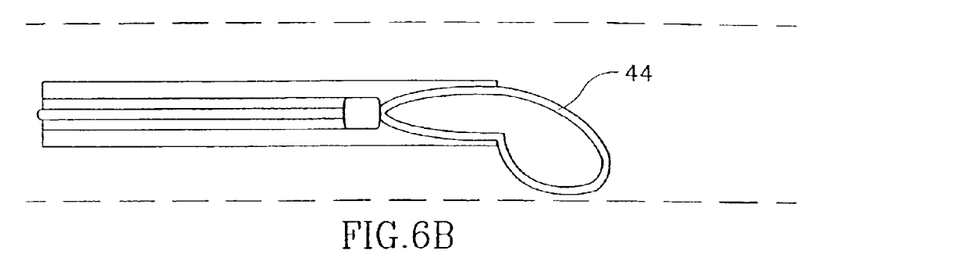
Figure 6C:
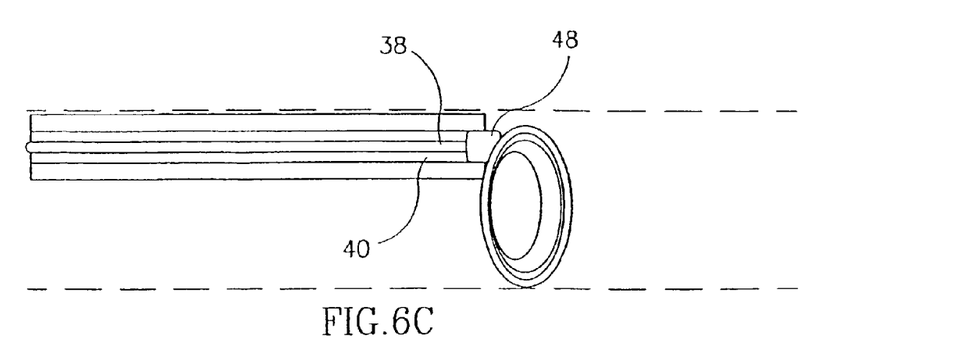
Figure 6D:
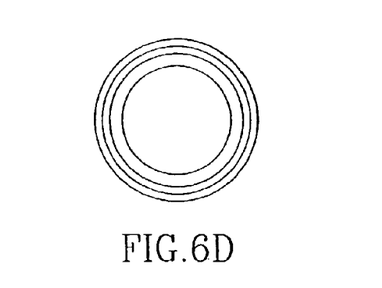

The delivery of the illustrated embodiment of the device to a desired location in a blood vessel is exemplified in FIGS. 6A-D. The device 34 is maintained in a collapsed conformation while in the delivery catheter 36. The delivery catheter contains within it a feeding catheter 38 enveloped by a release catheter 40. The delivery catheter is advanced in the artery 41 to the desired location in the blood vessel, at which the device 34 is extruded into the arterial lumen 42 (FIG. 6A). As the device 34 is advanced out of the catheter, the platform 44 expands to its preformed shape within the lumen 42 and attaches to the inner wall 46 of the artery (FIG. 6B). Once the ring is in its optimal position, the band is inflated through the feeding catheter.

The preformed shape of the ring is such that a ring is formed at a right angle to the axis of the delivery catheter (FIG. 6C). For example, the connection between the Nitinol ring and delivery system may be given a preformed shape of 90°. Alternatively, the delivery catheter may be angled at its end so that the ring protrudes at an angle when advanced out of the catheter.

Figure 9A:
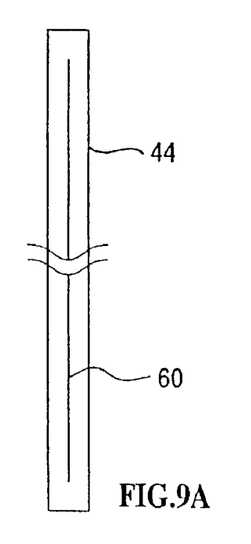
FIGS. 9A and 9B illustrate an implementation of a Nitinol ring particularly effective for achieving transverse deployment of the platform of the present invention relative to a deployment catheter, the ring being shown in a straight state prior to deployment and in its deployed state, respectively.
Figure 9B:
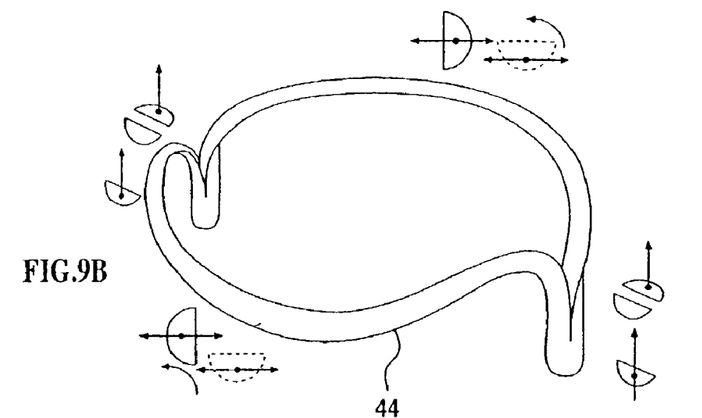
Figure 9C:
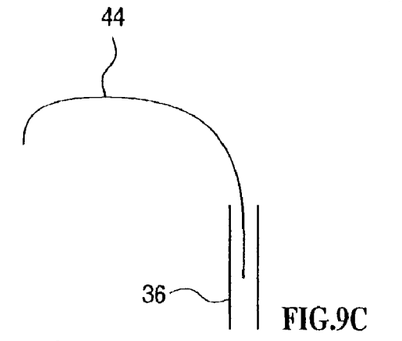
FIGS. 9C and 9D are a side view and a front view, respectively, showing the Nitinol ring of FIGS. 9A and 9B during deployment from a catheter.
Figure 9D:
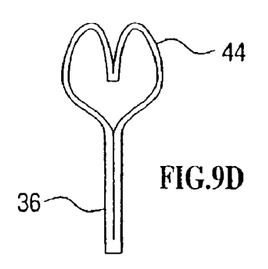
Figure 9E:
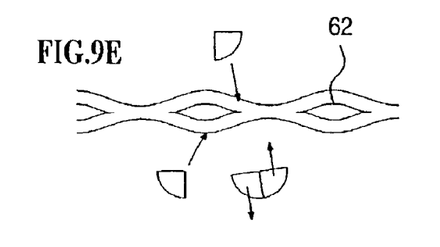
FIG. 9E is an enlarged view of a part of the ring of FIG. 9B showing an additional optional feature of the present invention.

FIGS. 9A-9E show a particularly preferred configuration of the Nitinol ring itself for implementing the aforementioned 90° turn on deployment of the platform 44. Specifically, the shape memory material is here preset to form resembling an open pair of jaws (FIG. 9B) exhibiting a roughly circular form in plan view while having roughly a C-shaped form in side view (FIG. 9C). The C-shaped curvature ensures the required transverse deployment as the device is gradually released from the delivery catheter 36 (FIGS. 9C and 9D).

Optionally, the structure illustrated in FIGS. 9A-9E may be implemented using an appropriately shape-set closed loop of Nitinol wire. Alternatively, in the preferred implementation as shown, the structure may be constructed from a single rod of Nitinol which is subdivided by a slit 60 running along a major part of its length but stopping short of its ends. This results in two separable lobes, each of roughly semicircular cross-section. Optionally, a torsional deformation may be included in the preset shape to ensure that the smoothly curved outer surface of each lobe faces outwards towards the vessel wall, thereby spreading loading. According to a further option, the semicircular cross-section lobes may themselves be subdivided by small slits 62 and biased to open up into a latticework type form (FIG. 9E) to further spread loading of the vessel wall.

If necessary, the feeding catheter may be left in place so that additional adjustments in the band diameter may be made. Once the dimensions of the device are finally established, the feeding catheter is pulled free from the collar which seals the fluid in the band. The device may be released from the catheter by advancing the release catheter 40 against the collar 48 while pulling back on the feeding catheter 38, thereby pushing the collar off the feeding catheter. The elastic collar then closes and the detached device (FIG. 6D) is implanted in the arterial wall. Other release mechanisms are of course possible, as will be clear to the skilled man of the art. For example, release of the ring independent of the feeding catheter may be achieved by having an attachment wire coaxial to the feeding catheter which can either unhook or unscrew from the ring.

In some cases, it is desirable to remove the device after a certain period of time. As stated above, prior art devices generally require surgery in order to remove them. The device of the invention, however, can be made 'breakable' or capable of being severed so that the band can be released in the same way in which it was inserted, i.e. by a transcatheter technique.

The connector is the weak link of the device which allows for the platform to be broken when it is no longer required. This can be achieved by passing a high pressure balloon catheter through the lumen in the center of the band and expanding the balloon. The ring will be breached due to the presence of a breakable section, and the fluid will leak out of the torn apart balloons. The Nitinol ring and silicone may then become part of the pulmonary arterial wall and become covered by endothelium (the inner lining). Or alternatively the band can be removed by a definitive surgical procedure.

Figure 7A:
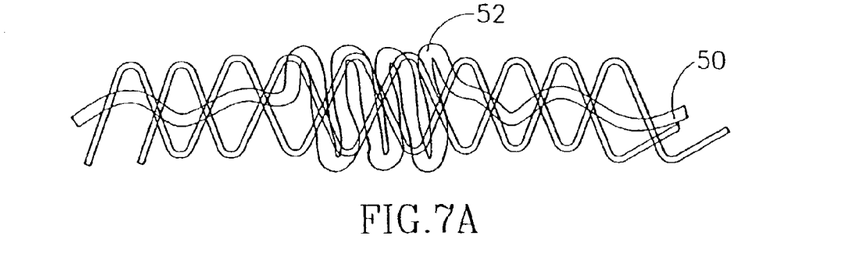
Figure 7B:
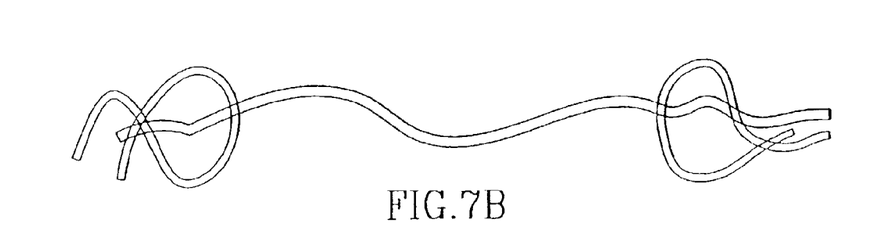

In order for the Nitinol ring to be 'breakable', a weak link may be created in the platform. One example is illustrated in FIG. 7. A thick Nitinol strand 50 is folded for a small distance creating an area 52 which can be unfolded and expanded 54 at a later stage during a catheterization procedure, by advancing a high pressure balloon of a larger diameter than the platform through the lumen of the band and expanding the balloon to the desired diameter.

Figure 8A:
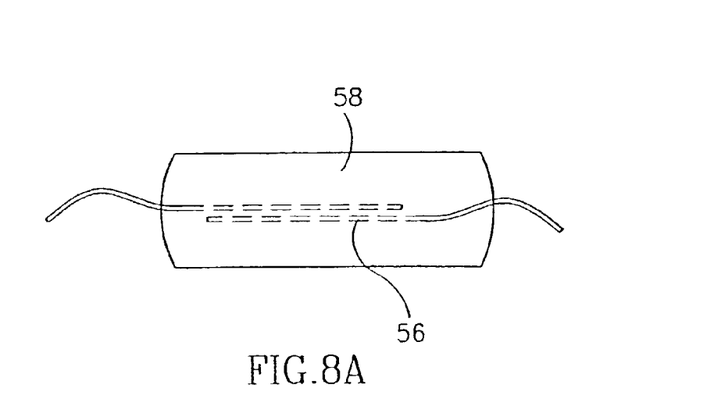
Figure 8B:
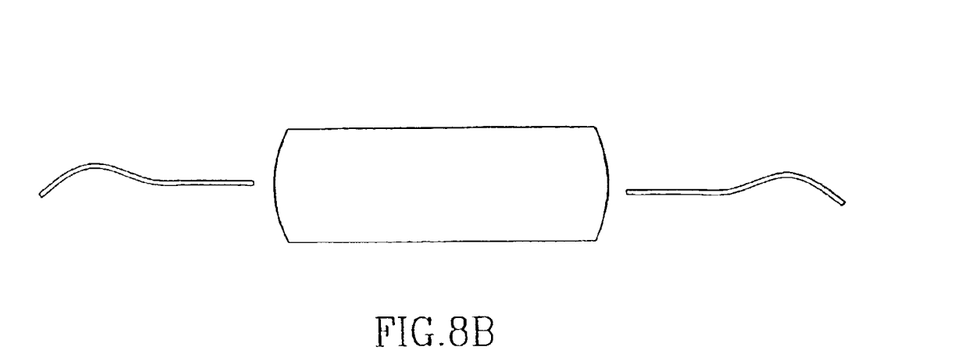

An alternative approach is illustrated in FIG. 8. The ends 56 of the thick Nitinol strand meet inside a stiff sleeve 58 in which they overlap but are not connected. The sleeve provides support for the broken platform by not allowing the platform to collapse or fold in on itself. However when the platform is expanded by a high pressure balloon, the ends of the Nitinol strand come apart. The balloons are broken at the connector.

A further embodiment of the device of the invention is a vena cava filter for pulmonary emboli. The device of the invention would comprise a platform as described above and a filter. The filter may be made of crosslinks of Nitinol wire attached to the filter and since these are made of shape memory alloy they can be folded easily into the delivery catheter. The fixation of the platform in situ would be by diffuse pressure of the ring on the vessel wall, preventing deep penetration of the hooks as described above with respect to the pulmonary band.

A still further embodiment using a platform of the invention could include a form of transcatheter cardiac or vessel valve. Examples of valves which could be mounted on the platform are pericardial valves, bovine, pig, etc. or synthetic material.

Although several preferred embodiments have been described above, the scope of the invention is defined by the following claims.

What is claimed is:

1. A combination of an untethered intravascular device and an associated deployment system for minimally invasive deployment of the untethered intravascular device within a vessel, the combination comprising:
    a delivery system having a lumen defining a feed direction; and
    an intravascular device having a retention configuration including at least one closed loop of flexible material deployed within said lumen in a first state in which said closed loop is folded on itself and substantially straightened so as to extend substantially parallel to said feed direction to allow delivery through said delivery system, said closed loop being further configured so as to be elastically biased to a predefined curved form such that, when said closed loop is advanced beyond said delivery system, said biasing to a curved form results in deployment of said loop in a direction generally perpendicular to said feed direction and opening of said loop to provide a formation for retention against an inner wall of the vessel,
    wherein said intravascular device is, after deployment, an untethered intravascular device configured such that said intravascular device is retained in a given position within the vessel primarily by contact of said at least one loop against the inner wall of the vessel, and wherein said formation for retention is substantially circular as viewed along said feed direction and at least partially curved as viewed along a direction perpendicular to said feed direction.

2. The combination of claim 1, wherein said untethered intravascular device is retained in said given position within the vessel exclusively by contact of said at least one loop against an inner wall of the vessel.

3. The combination of claim 1, wherein said retention configuration is a non-penetrative retention configuration.

4. The combination of claim 1, wherein said closed loop is formed from an alloy having superelastic properties at body temperature, said closed ring being pre-shaped to said formation for retention, said closed loop being subsequently deformed to assume said first state prior to insertion within said delivery system.

5. The combination of claim 4, wherein said alloy is Nitinol.

6. The combination of claim 1, wherein said untethered intravascular device includes an inflatable device mechanically linked to said closed loop.

7. The combination of claim 1, wherein said untethered intravascular device includes an intravascular filter structure mechanically linked to, or integrally formed with, said closed loop.

8. The combination of claim 1, wherein said untethered intravascular device includes a valve member mechanically linked to said closed loop.

9. The combination of claim 1, wherein said closed loop includes a breakable section.

10. The combination of claim 1, wherein a band is mounted on said closed loop.

11. The combination of claim 10, wherein said band includes at least one inflatable balloon.

12. The combination of claim 10, wherein the diameter of said band is adjustable.

13. The combination of claim 10, wherein said band is a pulmonary artery band.

* * * * *